United States Patent [19]

Ise et al.

[11] Patent Number: 5,573,761
[45] Date of Patent: Nov. 12, 1996

[54] AGENT FOR REDUCING NEPHROTOXICITY DUE TO MEDICINE

[75] Inventors: Michihito Ise, Saitama; Hideo Hayashi, Tokyo, both of Japan

[73] Assignee: Kureha Chemical Industry Co., Ltd., Tokyo, Japan

[21] Appl. No.: 556,084

[22] Filed: Nov. 9, 1995

[30] Foreign Application Priority Data

Nov. 15, 1994 [JP] Japan .................................. 6-305428

[51] Int. Cl.⁶ .................................................. A61K 33/44
[52] U.S. Cl. .................................................. 424/125
[58] Field of Search .................................................. 424/125

[56] References Cited

U.S. PATENT DOCUMENTS

| | | | |
|---|---|---|---|
| 3,934,007 | 1/1976 | Gussin et al. | 424/125 |
| 4,681,764 | 7/1987 | Endo et al. | 424/125 |
| 4,761,284 | 8/1988 | Nishimura et al. | 424/125 |

OTHER PUBLICATIONS

Domitsu et al., Surgery Today (Tokyo) 24(12), pp. 1068–1072, (Biosis abstract only).

Gotoh et al., Nippon Hinyokika Gakkai Zasshi (Japan), 81(9) pp. 1337–1342 (Medline abstract only).

Feun et al., Proc. Am. Assoc. Cancer Res. 26, 76 Meet., 263 (Derwent abstract only).

*Primary Examiner*—Raymond Henley, III
*Attorney, Agent, or Firm*—Sughrue, Mion, Zinn, Macpeak & Seas

[57] ABSTRACT

An agent for reducing nephrotoxicity due to a platinum complex compound, comprising an activated spherical carbon as an active ingredient is disclosed.

4 Claims, No Drawings

AGENT FOR REDUCING NEPHROTOXICITY DUE TO MEDICINE

BACKGROUND OF THE INVENTION

1. Field of the Invention

The present invention relates to an agent for reducing nephrotoxicity due to a platinum complex compound, particularly cisplatin, comprising an activated spherical carbon as an active ingredient, the use of an activated spherical carbon for reducing nephrotoxicity due to a platinum complex compound, particularly cisplatin, and a method of reducing nephrotoxicity due to a platinum complex compound, particularly cisplatin, comprising administering an effective amount of activated spherical carbon.

2. Description of the Related Art

Recently, chemotherapy for a cancer has rapidly progressed. Nevertheless, an antitumor agent acts not only on tumorous tissues, but also on normal tissues. Thus, adverse effects are inevitable. Therefore, there are many attempts to reduce the adverse effects.

Platinum complex compounds, particularly cisplatin, i.e., cis-dichloro-diamine-platinum, are excellent antitumor agents. A remarkable prolongation of life can be expected in testicular tumor, bladder cancer, pyeloureter tumor, kidney cancer, prostatic cancer, or ovarian cancer by administering such a compound. Main adverse effects of cisplatin are nephrotoxicity, gastrointestinal disorder, hemotoxicity, and neurotoxicity. In particular, the nephrotoxicity is the major dose-limiting adverse effect in a usual intravenous, intraarterial or intraperitoneal administration.

The nephrotoxicity is caused by cisplatin secreted in uniniferous tubules. The longer the high concentration of cisplatin is maintained, the severer nephropathy is caused. The degree of nephropathy may be determined by means of, for example, creatinine clearance. Sometimes, a severe symptom, such as renal insufficiency, is caused.

Cisplatin is generally administered under the diuretic condition. It is managed to reduce the nephrotoxicity by lowering the concentration of cisplatin in uniniferous tubules. The diuretic condition may be produced by adding water and administering diuretic agent, such as mannitol or furosemide. It is also known that systemic adverse effects due to cisplatin administration can be reduced, using a hemoperfusion column charged with activated carbon, in combination therewith. Feun et al. disclosed experiments wherein activated charcoals were orally administered to dogs after the intravenous administration of cisplatin to the dogs (Proc. Am. Assoc. Cancer Res., 1985, vol. 26, No. 1039).

Japanese Unexamined Patent Publication (Kokai) No. 6-192109 enumerates sodium thiosulfate, acetazolamide, selenium dioxide, sodium selenate, cysteine, 3-aminobenzamide, fosfomycin, S-adenosy-L-methionine and so on, as compounds which can reduce the nephrotoxicity due to cisplatin.

However, the administration under the diuretic condition or the combined use of the hemoperfusion column charged with activated carbon inflicts a pain on a patient, and the nephrotoxicity was not satisfactorily reduced. The Feun et al. reference only discloses the prolongation effect of life, but does not disclose the reduction of the nephrotoxicity. Of the compounds enumerated in said Japanese publication, no compound has been put to clinical use. Therefore, there was a desire to develop an agent for definitely reducing the nephrotoxicity caused by cisplatin administration.

SUMMARY OF THE INVENTION

The present invention is completed in view of the above problems. The object of the present invention is to provide an agent for reducing the nephrotoxicity due to a platinum complex compound, which agent can definitely reduce the nephrotoxicity caused by administering a platinum complex compound, without forced addition of water or forced administration of diuretic agent to a patient, without inflicting a pain on a patient, while the antitumor action of the platinum complex compound, particularly cisplatin, is maintained.

The inventors of the present invention engaged in intensive studies on active substances different from the conventional agent to solve the above problems, and as a result, have found that the nephrotoxicity can be definitely reduced by orally administering activated carbon composition for medical use during the cisplatin administration. The present invention is based on the findings.

Accordingly, the object of the present invention is to provide a nephrotoxicity-reducing agent.

Other objects and advantages will be apparent from the following description.

In accordance with the present invention, there is provided an agent for reducing nephrotoxicity due to a platinum complex compound, which agent comprises activated spherical carbon as an active ingredient and a pharmaceutically acceptable carrier or diluent.

DESCRIPTION OF THE PREFERRED EMBODIMENTS

The present invention will be explained in detail hereinafter.

The activated spherical carbon used as the active ingredient in the agent for reducing the nephrotoxicity caused by a platinum complex compound according to the present invention is not particularly limited so long as it comprises activated carbon particles having a spherical shape that can be orally administered for medical treatment. The activated spherical carbon that has excellent adsorbability is preferable. A particle diameter of the activated spherical carbon used in the present invention ranges preferably 0.05 to 2 mm, more preferably 0.1 to 1 mm. A specific surface area of the activated spherical carbon used in the present invention ranges preferably 500 to 2000 $m^2/g$, more preferably 700 to 1500 $m^2/g$. A void volume for pores having a radius of 100 to 75000 Angstroms in the activated spherical carbon used in the present invention ranges preferably 0.01 to 1 ml/g, more preferably 0.05 to 0.8 ml/g. It is noted that the specific surface area is determined by means of a methanol adsorption method using an automatically measuring apparatus of an amount of the adsorbed material, and the void volume is determined by means of a mercury porosimeter.

A medical powdery activated carbon conventionally used as an antidote has the side effect to easily cause constipation. Constipation during illness is particularly dangerous, and thus the above point is a major defect. The activated spherical carbon is advantageous, in comparison with the powdery activated carbon, in that the former does not fly away all around, or does not cause constipation even if continuously administered. When the particle diameter of the activated spherical carbon used in the present invention is less than 0.05 mm, the function to eliminate side effects, such as constipation, is not sufficient. When the particle diameter is over 2 mm, not only administration becomes difficult, but also the desired pharmacological effect is not obtained quickly.

The shape of the spherical carbon is one of the important factors for obtaining the effect of the present invention, and must be substantially spherical. The activated spherical carbon obtained from petroleum pitches as mentioned below is preferably used in the present invention, because its shape is nearly a solid-geometrically real sphere.

In the production of the activated spherical carbon used in the present invention, any raw material which activated carbon is obtained from, for example, sawdust, coal, coconut shells, petroleum pitches, coal pitches, or synthetic organic high polymers, may be used. The activated spherical carbon may be prepared, for example, by carbonizing the starting material and then activating the carbonized material. As the method for activation, it is possible to use various known methods for activation with, for example, steam, chemicals, air, and carbon dioxide gas, so long as pharmaceutically acceptable purity is maintained.

The activated spherical carbon includes, for example, granulated-activated carbon obtained from powdery carbonaceous materials, activated spherical carbon obtained by calcinating organic polymer materials, and activated spherical carbon obtained from petroleum hydrocarbons (petroleum pitches).

The granulated-activated carbon from powdery carbonaceous materials may be prepared, for example, by granulating powdery carbonaceous materials into small spheres with a binder, such as tar or pitch, carbonizing the small spheres under an inert atmosphere at 600° to 1000° C., and then, activating the carbonized spheres. As the method for activation, it is possible to use various known methods for activation with, for example, steam, chemicals, air, and carbon dioxide gas. The activation with steam is carried out, for example, under a steam atmosphere at 800° to 1100 ° C.

The activated spherical carbon obtained by calcinating organic polymer materials is disclosed in, for example, Japanese Examined Patent Publication (Kokoku) No. 61-1366, and may be prepared, for example, by mixing condensation-type or polyaddition-type thermosetting prepolymer materials with curing agent, curing catalyst, emulsifying agent and so on, and performing reaction at room temperature or with warming, under stirring. The reaction mixture becomes first suspended, and a continuous stirring procedure results in spheres of thermosetting resin. After collected, the spheres are carbonized by heating under an inert atmosphere at 500° C. or more, and activated by one of the above methods to obtain the desired activated spherical carbon of the calcinated organic polymer material.

The activated spherical carbon obtained from petroleum pitches has a diameter of preferably 0.05 to 2 mm, more preferably 0.1 to 1 mm, a specific surface area of preferably 500 to 2000 $m^2/g$, more preferably 700 to 1500 $m^2/g$, and a void volume (for pores having a radius of 100 to 75000 Angstroms) of preferably 0.01 to 1 ml/g. The activated spherical carbon obtained from petroleum pitches may be prepared, for example, by the following two methods.

The first method comprises, as disclosed in, for example, U.S. Pat. No. 3,917,806 [Japanese Examined Patent Publication (Kokoku) No. 51-76] and U.S. Pat. No. 4,761,284 [Japanese Unexamined Patent Publication (Kokai) No. 54-89010], forming small spherical particles of molten pitches, rendering the particles infusible with oxygen, carbonizing the particles by baking in an inert atmosphere at 600° to 1000° C.; and then activating the carbonized particles in a steam atmosphere at 850° to 1000° C. The second method comprises, as disclosed, for example, in U.S. Pat. No. 4,420,433 [Japanese Examined Patent Publication (Kokoku) No. 59-10930], forming strings of molten pitches, crushing the strings, introducing the crushed pitches into hot water to form spherical particles, rendering the particles infusible with oxygen, and then carbonizing and activating the infusible particles in the same manner as the first method.

In the present invention, activated spherical carbon which is further treated with ammonia, or subjected to an oxidizing and/or reducing treatment may be used as the active ingredient. The ammonia, oxidizing and/or reducing treatment may be applied to any one of the above-mentioned granulated-activated carbon obtained from powdery carbonaceous materials, activated spherical carbon obtained by calcinating organic polymer materials, and activated spherical carbon obtained from petroleum pitches.

The ammonia treatment comprises, for example, treating the activated spherical carbon with an aqueous ammonia containing 1 to 1000 ppm ammonia, in a ratio of aqueous ammonia/activated spherical carbon of 2 to 10 (v/v) at 10° to 50° C. for 0.5 to 5 hours. Examples of the activated spherical carbon obtained by treating the petroleum pitch-activated spherical carbon with ammonia are disclosed in, for example, U.S. Pat. No. 4,761,284 [Japanese Unexamined Patent Publication (Kokai) No. 56-5313]. The ammonia-treated activated spherical carbon has, for example, a diameter of 0.05 to 2 mm, preferably 0.1 to 1 mm, a specific surface area of 500 to 2000 $m^2/g$, preferably 700 to 1500 $m^2/g$, a void volume (for pores having a radius of 100 to 75000 Angstroms) of 0.01 to 1 ml/g and pH of 6 to 8.

The above oxidizing treatment means a heating treatment at a high temperature in an oxidizing atmosphere containing oxygen. As the source of oxygen, pure oxygen, nitrogen oxide, air, or the like may be used. Further, the above reducing treatment means a heating treatment at a high temperature in an atmosphere inert to carbon. The inert atmosphere to carbon may be formed, using nitrogen, argon, helium, or mixtures thereof.

The oxidizing treatment is carried out in an atmosphere containing preferably 0.5 to 25% by volume of oxygen, more preferably 3 to 10% by volume of oxygen, and the temperature of preferably 300° to 700° C., more preferably 400° to 600° C. The reducing treatment is preferably carried out in the inert atmosphere at a temperature of 700° to 1100° C., more preferably 800° to 1000° C.

Examples of the activated spherical carbon obtained by oxidizing and/or reducing the petroleum pitch-activated spherical carbon are spherical carbonaceous adsorbents disclosed in, for example, U.S. Pat. No. 4,681,764 [Japanese Examined Patent Publication (Kokoku) No. 62-11611]; "KUREMEZIN" (trade name: Kureha Chemical Industry Co. Ltd.) and the encapsulated formulation thereof, i.e., "KUREMEZIN Capsule 200" (trade name: Kureha Chemical Industry Co. Ltd.) (200 mg/cap).

The above-mentioned "KUREMEZIN" is an oral adsorbent comprising homogeneous fine spherical porous carbon particles having a diameter of about 0.2 to 0.4 mm, and is clinically used as a medicine effective in improvement of uremic symptom and postponement of dialysis commencement, in progressive chronic renal insufficiency.

The activated spherical carbon obtained by further oxidizing and/or reducing the activated spherical carbon has preferably a diameter of 0.05 to 2 mm, more preferably 0.1 to 1 mm, a specific surface area of 500 to 2000 $m^2/g$, more preferably 700 to 1500 $m^2/g$, a void volume (for pores having a radius of 100 to 75000 Angstroms) of 0.01 to 1 ml/g.

The medical agent which causes the nephrotoxicity that the agent according to the present invention can reduce is platinum complex compound, for example, cisplatin, dichloroethylenediamine-platinum (II), 1,2-diamino-cyclohexyl-platinum (II)-malonate or -sulfate, carboplatin, diisopropylamino-trans-dihydroxy-cis-dichloro-platinum (IV), (-)-(R)-2-aminomethylpyrrolidine(1,1-cyclobutanecarboxylate)platinum (II)-monohydorate, cis-diamineglycolate platinum, cisplatin, i.e., cis-dichlorodiamine platinum, is preferable. The nephrotoxicity which can be reduced by the agent of the present invention is a decline in the renal function caused by dysfunction of kidney cells.

The inventors of the present invention have discovered that when an activated carbon formulation for medical use, i.e., the above-mentioned oxidation and reduction treated-activated spherical carbon from petroleum pitches was orally administered to normal rats during administering a platinum complex compound, i.e., cisplatin, the nephrotoxicity due to cisplatin was surprisingly reduced to a considerable extent. Further, no side effect was observed in the administration of the activated spherical carbon. Consequently, it is manifest that a preparation containing the activated spherical carbon as an active ingredient is effective as an agent for reducing the nephrotoxicity caused by a platinum complex compound. The administering route of the active spherical carbon may be different from that of the platinum complex compound. Therefore, the nephrotoxicity due to the platinum complex compound can be reduced, without degrading antitumor action thereof.

According to the present invention, the agent for reducing the nephrotoxicity due to a platinum complex compound may be administered to a mammal including a human who is or may be affected with the nephrotoxicity caused by administering a platinum complex compound, particularly cisplatin. The nephrotoxicity-reducing agent of the present invention preferably is administered orally. The dosage thereof depends on, for example, the subject (a mammal, particularly a human), age, individual differences, and/or disease conditions. For example, the dosage in the case of a human is usually 0.2 to 20 g of activated spherical carbon per day. The dosage may be suitably adjusted depending on the state of the disease. The daily dosage may be taken up once or divided into several times. The activated spherical carbon may be administered as it is, or in the form of a pharmaceutical composition. The activated spherical carbon may be administered in the form of a slurry suspended in potable water.

The time when the nephrotoxicity-reducing agent of the present invention is administered may be appropriately selected with respect to the administration time of the platinum complex compound. For example, the nephrotoxicity-reducing agent may be administered before, during or after the administration of the platinum complex compound, or the former administration may be partially overlapped with the latter administration. Further, such administration schedules may be suitably combined or repeated. It is preferable that the period of administering the nephrotoxicity-reducing agent according to the present invention overlaps with, or is in conformity with the period of administering the platinum complex compound.

The activated spherical carbon formulation may be administered in any forms, such as granules, tablets, sugar-coated tablets, capsules, stick packages, divided packages, suspensions, or the like. In the case of capsules, the usual gelatine capsules, or if necessary, enteric capsules may be used. In the case of granules, tablets, or sugar-coated tablets, these formulations must be broken down into the original fine particles in the alimentary canal of a patient. The amount of the activated spherical carbon contained in the formulation is generally 1 to 100% by weight. The preferred formulation of the activated spherical carbon of the present invention is a capsule, stick package, or divided package. The activated spherical carbon is incorporated into said formulation, as it is.

EXAMPLES

The present invention will now be further illustrated by, but is no means limited to, the following Examples.

Preparation Example 1: Preparation of Activated Spherical Carbon

Pitch (75 kg) (softening point= 182° C.; insolubles in quinoline= 10% by weight; ratio of hydrogen atoms/carbon atoms= 0.53) prepared by pyrolytrically decomposing naphtha, and naphthalene (25 kg) were charged into a 300 liter autoclave equipped with stirring wings, melted by heating at 210° C., and mixed. The pitch mixture was cooled at 80° to 90 ° C. to adjust the viscosity suitable for extrusion-spinning, and then, extruded under pressure of 50 kg/cm$^2$ at a rate of 5 kg/min from an extruder head with 100 pores having a diameter of 1.5 mm. The string-like extruded pitches were conveyed through a plastic watershoot inclined at about 40° into a cooling tank at 10° to 25° C. Water was flushed downwards at 3.0 m/sec in the watershoot, and thus, the extruded pitches were continuously stretched on the way to the cooling tank, immediately after the extrusion. In the cooling tank, many string-like pitches having a diameter of 500 μm were accumulated. The string-like pitches were allowed to stand in water for about 1 minute to solidify, and thus, the state was converted to that easy to be broken by hand. The resulting pitches were charged in a high-speed cutter, and water was added thereto. After stirring for 10 to 30 seconds, the string-like pitches were completely shattered to obtain bar-like (cylindrical) pitches. The ratio of the height to the diameter of the cylinder was found to be 1.5 in average by a microscope.

After the bar-like pitches were filtered, 100 g of the bar-like pitches were poured into 1 kg of 0.5% polyvinyl alcohol aqueous solution heated at 90° C., melted, suspended with stirring, and cooled to obtain spherical particles. After a major part of water was filtered out, the resulting spherical particles were charged into an extractor. Hexane was passed through the particles to extract and remove the naphthalene, and the particles were dried with air. Thereafter, the particles were heated on a fluid bed with heated air passed therethrough by heating up to 300° C. at a rate of 25° C./h, then allowed to stand further at 300° C. for 2 hours and thus rendered infusible. Then, the infusible particles were heated up to 900° C. in steam, allowed to stand at 900° C. for 2 hours in steam, and carbonized and activated, whereby porous activated spherical carbon were obtained. The diameter of the resulting activated spherical carbon was 0.05 to 1.0 mm. The resulting activated spherical carbon particles were then treated for 3 hours at 600° C. in an atmosphere of a 3% oxygen on a fluid bed, then heated to 950° C. in a nitrogen atmosphere and maintained at 950° C. for 30 minutes to obtain the petroleum pitch-activated spherical carbon further with oxidation and reduction treatment (hereinafter referred to as the "specimen 1"). The diameter of the resulting petroleum pitch-activated spherical carbon further with oxidation and reduction treatment was 0.05 to 1 mm.

In an acute toxicity test by orally administering the petroleum pitch-activated spherical carbon further with oxidation and reduction treatment to rats (Cpb; WU; Wistar Random), no abnormalities were observed even with the maximum dosage (5000 mg/kg for male and female rats) according to the Guidelines for Toxicity Studies of Drugs (Notification No. 118 of the Pharmaceutical Affairs Bureau, Ministry of Health and Welfare, Japanese Government, Feb. 15, 1984).

Pharmacological Example: Effect of Activated Spherical Carbon Administration on Reduction of Cisplatin Nephrotoxicity In this Example, the "specimen 1" prepared in Preparation Example 1 was used as active spherical carbon. To twenty-two Wistar male rats (body weights= 300 to 400 g), cisplatin was intraperitoneally administered twice a week for 13 weeks at the dosage of 1 mg/kg/day. At the beginning of the 14th week, 22 rats were divided into two groups consisting of 11 rats respectively, in a manner that there was no imbalance therebetween. For 10 weeks from the beginning of the 14th week to the beginning of 24th week, normal feeds were given to 11 rats belonging to a control group, whereas the "specimen 1" was orally administered at 1.0 to 1.4 g/day/rat in addition to normal feeds to 11 rats belonging to an active spherical carbon group. Further, cisplatin was intraperitoneally administered twice a week for 10 weeks from the beginning of the 14th week to the beginning of 24th weeks at the dosage of 0.5 mg/kg/day. At the 24th week, the renal function was determined by means of creatinine clearance to evaluate the nephrotoxicity. Because cisplatin causes disorder in uriniferous tubules in a kidney, the uriniferous tubules of the rats were pathologically examined. Statistical test between the groups was conducted by t test.

At the 24th week, creatinine clearance (average ± standard deviation) was found to be 0.63±0.39 ml/min for the control group, and 1.09±0.48 ml/min for the active spherical carbon group. There was observed a statistically significant difference ($p < 0.05$) therebetween. In other words, renal function in the active spherical carbon group was maintained significantly in a statistical viewpoint, and the nephrotoxicity due to cisplatin was reduced. Further, the pathological examination revealed that the tubular lesion was clearly inhibited.

Formulation Example 1: Formulation of Capsules

Capsules were prepared by sealing 200 mg of the activated spherical carbon obtained in Preparation Example 1 in gelatine capsules.

Formulation Example 2: Formulation of Stick Packages

Stick packages were prepared by filling 2 g of the activated spherical carbon obtained in Preparation Example 1 into stick-containers of laminated film, and then heat-sealing the containers.

The nephrotoxicity caused by administering a platinum complex compound can be definitely reduced by orally administering the nephrotoxicity-reducing agent of the present invention.

Although the present invention has been described with reference to specific embodiments, various changes and modifications obvious to those skilled in the art are deemed to be within the scope and concept of the invention.

What is claimed is:

1. A method for reducing nephrotoxicity caused by a platinum complex compound while retaining anti-tumor activity of said platinum complex compound, comprising the step of administering an effective amount of an activated spherical carbon to a mammal during treatment of said mammal with said platinum complex compound, wherein said method is carried out without forced addition of water or administration of a diuretic to said mammal.

2. A method according to claim 1, wherein said platinum complex compound is cisplatin.

3. A method according to claim 1, wherein said activated spherical carbon has an diameter of 0.05 to 2 mm.

4. A method according to claim 1, wherein said activated spherical carbon is orally administered.

* * * * *